United States Patent [19]

Kojima et al.

[11] Patent Number: 5,426,033
[45] Date of Patent: Jun. 20, 1995

[54] METHOD FOR ENZYMATIC DETERMINATION OF SUBSTRATE AFTER ENZYMATICALLY REMOVING GALACTOSE

[75] Inventors: Ayako Kojima; Norihito Aoyama; Akira Miike, all of Shizuoka, Japan

[73] Assignee: Kyowa Medex Co., Ltd., Tokyo, Japan

[21] Appl. No.: 186,045

[22] Filed: Jan. 25, 1994

[30] Foreign Application Priority Data

Jan. 27, 1993 [JP] Japan ................................. 5-011925

[51] Int. Cl.[6] ........................... C12Q 1/54; G01N 1/00
[52] U.S. Cl. ......................................... 435/14; 435/25; 435/26; 435/28; 435/39; 436/174; 436/175
[58] Field of Search ..................... 435/14, 25, 26, 39, 435/28; 436/174, 175

[56] References Cited

U.S. PATENT DOCUMENTS

| | | | |
|---|---|---|---|
| 4,220,503 | 9/1980 | Johnson | 435/25 |
| 4,409,328 | 10/1983 | Zeigenhorn et al. | 435/25 |
| 4,810,640 | 3/1989 | Nakamura et al. | 435/25 |
| 4,994,377 | 2/1991 | Nakamura et al. | 435/25 |

FOREIGN PATENT DOCUMENTS

| | | |
|---|---|---|
| 0261591 | 3/1988 | European Pat. Off. . |
| 4242794 | 6/1993 | Germany . |
| 4321807 | 1/1994 | Germany . |
| 163482 | 10/1982 | Japan . |
| 2-104298 | 4/1990 | Japan . |

OTHER PUBLICATIONS

Hammerstedt et al, *The Journal of Biological Chemistry*, vol. 258, No. 14, pp. 8759–8768, Jul. 25, 1983.
Pudek et al, *Clin. Biochem.*, vol. 23, No. 3, pp. 221–223, Jun. 1990.
Ueda et al, *Chemical Abstracts*, vol. 118, p. 419, Ref. #120446b, 1993 (JP04, 346, 798 (92, 346, 798) 02 Dec. 1992).
Derwent Abstract 89–056219/08 (JP 1-6756).
Derwent Abstract 90–161279/21 (JP 2-104298).
Derwent Abstract 84–277529/45 (EPO 124287).
Derwent Abstract 80133 D/44 (EPO 38205).

*Primary Examiner*—William H. Beisner
*Assistant Examiner*—Abdel A. Mohamed
*Attorney, Agent, or Firm*—Fitzpatrick, Cella, Harper & Scinto

[57] ABSTRACT

A method for quantitating accurately 1,5-anhydroglucitol, fructose or amylase in a sample that contains galactose using an enzymatic determination involves a pretreatment which removes galactose from the sample by an enzyme reaction in which galactose is a substrate.

4 Claims, 4 Drawing Sheets

METHOD FOR ENZYMATIC DETERMINATION OF SUBSTRATE AFTER ENZYMATICALLY REMOVING GALACTOSE

BACKGROUND OF THE INVENTION

The present invention relates to a method for the quantitative determination of a specific component in a sample using an enzyme reaction. The method of the present invention is useful in clinical assays.

When quantitatively determining a specific component in a biological sample using an enzyme reaction, galactose present in the sample often disturbs accurate determination of the specific component. In such cases, prior to the quantitative determination, galactose is preferably first decomposed or converted into a substance which does not disturb the determination.

Previous methods for decomposing or converting galactose in samples include methods in which galactose is separated by ion exchange column chromatography disclosed in EP-A-261591 (U.S. Pat. No. 4,994,377) and Japanese Published Unexamined Patent Application No. 6756/89. However, these column chromatographic methods involve complicated procedures, and are unsuitable for clinical assays.

The level of 1,5-anhydroglucitol in human samples is known as a diagnostic marker for diabetes. EP-A-213279 (U.S. Pat. No. 4,810,640) discloses a method for quantitatively determining 1,5-anhydroglucitol which comprises: (1) reacting 1,5-anhydroglucitol in a sample with oxidase, and (2) determining the amount of the oxygen consumed, the hydrogen peroxide formed, or the reductant of an electron acceptor formed as a result of the oxidase reaction. However, oxidases using 1,5-anhydroglucitol as substrate have low substrate specificity, and they also react with galactose in the samples. Therefore, it is undesirable to apply these methods to samples containing a large amount of galactose.

SUMMARY OF THE INVENTION

In accordance with the present invention, a specific component to be determined in a sample containing galactose can be accurately determined by: converting galactose into a substance which does not disturb the determination by utilizing an enzyme reaction in which galactose is used as the substrate; and thereafter determining the specific component by using another enzyme reaction.

DETAILED DESCRIPTION OF THE INVENTION

Figure 1:
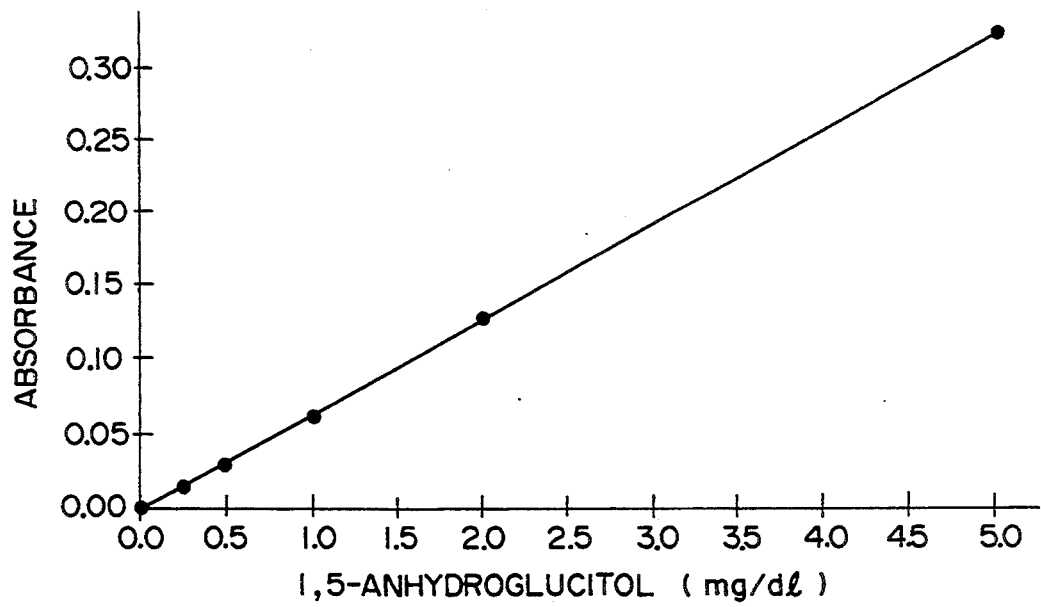
FIG. 1 shows the calibration curve for 1,5-anhydroglucitol obtained by the galactokinase method in combination with the hexokinase method.

The conversion of galactose into a substance which does not disturb the determination of the specific component can be achieved by an enzyme reaction wherein galactose is used as the substrate, for example, a reaction utilizing the action of galactokinase (EC 2.7.1.6) in the presence of adenosine triphosphate (ATP); a reaction utilizing the action of galactose dehydrogenase (EC 1.1.1.48; EC 1.1.1.120) in the presence of nicotinamide adenine dinucleotide phosphate (NADP) or nicotinamide adenine dinucleotide (NAD); and a reaction utilizing the action of galactose oxidase (EC 1.1.3.9) in the presence of oxygen.

The present invention is effective in all cases where the quantitative determination of the specific component in a sample by an enzyme reaction is made less accurate by the presence of galactose in the sample. That is, the method of the present invention can be effectively applied when the quantitative determination of the specific component utilizes an enzyme which also acts on galactose. The method of the present invention may also be applied effectively when the quantitative determination of the specific component generates galactose.

1,5-Anhydroglucitol is an example of a case in which the enzyme used for the quantitative determination also acts on galactose. Fructose and amylase are examples of a case in which the enzyme used for the quantitative determination generates galactose [Kyowa Medex products information, p.111–112, published by Kyowa Medex Co., Ltd. (1991)].

The method of the present invention is explained in detail below. A sample which may contain galactose is added to a buffer solution, and to this mixture are added (1) 0.1–10 mg/ml ATP and 1–100 units/ml galactokinase (EC 2.7.1.6) (galactokinase method), (2) 0.1–10 mg/ml NAD and 1–100 units/ml galactose dehydrogenase (EC 1.1.1.48) (NAD-dependent galactose dehydrogenase method), (3) 0.1–10 mg/ml NADP and 1–100 units/ml galactose dehydrogenase (EC 1.1.1.120) (NADP-dependent galactose dehydrogenase method), or (4) 1–100 units/ml galactose oxidase (EC 1.1.3.9) in the presence of oxygen (galactose oxidase method), to carry out a reaction at 5°–40° C. for 1–30 minutes, preferably 3–10 minutes. Ideally, the reaction is carried out for a sufficient time to ensure that at most only a trace amount of galactose remains in the sample. The above enzymes and their substrates are all commercially available and easily acquirable.

As the buffer solution, buffer solutions of pH 5–10 such as a phosphate buffer solution, a Tris-HCl buffer solution, and a Good's buffer solution may be used. To the buffer solution may be added, if necessary, a salt such as sodium chloride, a stabilizer such as albumin, and a metal such as manganese, magnesium or cobalt. In the specific embodiment using galactose oxidase, the oxygen already dissolved in the buffer solution is usually adequate. However, additional oxygen may be provided by aeration if necessary.

By the enzyme reactions described above, galactose in the sample is converted to gatactose-1-phosphate (galactokinase method); galactone-1,4-lactone (NAD-dependent or NADP-dependent galactose dehydrogenase method); or galacto-hexodialdose (galactose oxidase method). In the galactokinase method, an ATP production system such as pyruvate kinase (0.5–50 U/ml) and phosphoenol pyruvate (0.1–10 mg/ml) (Japanese Published Unexamined Patent Application No. 104298/90) or creatine kinase (1–100 U/ml) may be added to produce ATP in the reaction mixture, whereby the amount of ATP to be added can be minimized.

After galactose is eliminated by pretreatment using the enzyme reaction, a reagent necessary for the quantitative determination of the component to be determined is added to the sample. Then the component is quantitatively determined either by measuring the amount of the product of enzyme reaction or by measuring the change of the amount of a substance known to be utilized by the enzyme reaction.

The enzyme reaction for galactose elimination may preferably be combined with the glucose-elimination method disclosed in Japanese Published Unexamined Patent Application No. 104298/90 or a glucose-elimination method in which hexokinase, phosphohexose isomerase and 6-phosphofructokinase are made to act on glucose in the presence of ATP to convert glucose to fructose-1,6-diphosphate (hexokinase method). After both galactose and glucose are eliminated from the sample, the subsequent determination of the specific component can then be carried out optimally.

In the method of Japanese Published Unexamined Patent Application No. 104298/90, glucose existing in the sample to be determined is efficiently removed by treating the sample with Mg ion, ATP, phosphoenolpyruvic acid and pyruvate kinase, and hexokinase or glucokinase.

For the elimination of glucose by the hexokinase method, adenosine triphosphate, hexokinase, phosphohexose isomerase and 6-phosphofructokinase are added to the glucose-containing sample, and the reaction is carried out at 15°–50° C. for 1–30 minutes, preferably 3–10 minutes, in the presence of a magnesium salt if necessary.

In the hexokinase method, the enzymes and their amounts to be used are 0.5–50 U/ml hexokinase (EC 2.7.1.1) or hexokinase Type IV (glucokinase: EC 2.7.1.2) as hexokinase, 1–100 U/ml D-glucose-6-phosphate-ketol isomerase (EC 5.3.1.9) as phosphohexose isomerase, and 1–100 U/ml phosphohexokinase (EC 2.7.1.11) as 6-phosphofructokinase. All of these enzymes are commercially available and easily acquirable. In addition, ATP is used at a concentration of 0.1–10 mg/ml.

As a representative embodiment of the present invention, the quantitative determination of 1,5-anhydroglucitol in the sample is described below. Of course, the present invention may also be utilized in the quantitative determination of any other specific component, the accuracy of which is otherwise disturbed by the presence of galactose.

The determination of 1,5-anhydroglucitol may be carried out by any known method therefor. For example, 1,5-anhydroglucitol is acted on by oxidase and the resulting hydrogen peroxide is reacted with a chromogen in the presence of peroxidase. Then the amount of 1,5-anhydroglucitol is determined by measuring the absorbance of the reaction solution in the visible region.

As the oxidase, sorbose oxidase (EC 1.1.3.11) (10–1000 U/ml), pyranose oxidase (EC 1.1.3.10) (1–100 U/ml), and the like may be used. Peroxidase (EC 1.11.1.7) is used at a concentration of 1–100 U/ml. As the buffer solution, those which are described above may be used.

As the chromogen, any compound which produces a color when oxidized in the presence of peroxidase can be used. For example, a coupling system may be used which comprises 4-aminoantipyrine or 3-methyl-2-benzothiazolinonehydrazone, and phenol or a derivative thereof or aniline or a derivative thereof. Particularly, a substance which produces a highly sensitive pigment is preferred, and examples thereof include 2,2′-azino-bis(3-ethylbenzothiazoline-6-sulfonic acid), bis [3-bis(4-chlorophenyl)methyl-4-dimethylaminophenyl]amine (hereinafter "BCMA") (EP-A-124287), bis[3-bis(4-chlorophenyl)methyl-4-carboxyethylaminophenyl] amine (EP-A-124287), 10-N-methylcarbamoyl-3,7-dimethylamino-10H-phenothiazine (hereinafter "MCDP") (EP-A-38205) and 10-N-carboxymethylcarbamoyl-3,7-dimethylamino-10H-phenothiazine (hereinafter "CCAP") (EP-A-38205). The amount of the chromogen to be used is 1–1000 molar equivalents based on the hydrogen peroxide.

The reaction is carried out at 15°–50° C. for 3–30 minutes, preferably 5–10 minutes.

The effect of the present invention is demonstrated by the following test examples.

In general, the 1,5-anhydroglucitol and galactose contents of normal serum are about 2 mg/dl and 1 mg/dl, respectively. However, the galactose level in abnormal serum obtained from patients is as high as 30 mg/dl and the presence of galactose at such high level disturbs quantitative determination of 1,5-anhydroglucitol. Therefore, a process which can decompose over 30 mg/dl galactose is clinically useful. In order to show the effect of the method of the present invention, the following experiments were performed under the conditions that the 1,5-anhydroglucitol content was 2 mg/dl (the same level as normal serum) and the galactose content was 100 mg/dl (about three times the level of abnormal serum).

TEST EXAMPLE 1

The experiment was carried out using three types of samples: (1) purified water, (2) 2 mg/dl 1, 5-anhydroglucitol, and (3) 2 mg/dl 1,5-anhydroglucitol containing 100 mg/dl galactose. The amount of 1,5-anhydroglucitol in the test samples was determined by the methods described in Example 1 (combination of the galactokinase method and the hexokinase method), Example 3 (combination of the NAD-dependent galactose dehydrogenase method and the hexokinase method), Example 5 (combination of the NADP-dependent galactose dehydrogenase method and the hexokinase method), and Example 7 (combination of the galactose oxidase method and the hexokinase method). As a control experiment, the amount of 1, 5-anhydroglucitol in the test samples was determined by the same method as in Example 1 except that galactokinase was not contained in Reagent solution 1 (the hexokinase method alone). The results are shown in Table 1.

TABLE 1

| Method of pretreatment: Hexokinase method + | 1,5-anhydroglucitol content (mg) (OD value) | | |
|---|---|---|---|
| | Blank | 2 mg 1,5-anhydroglucitol | 2 mg 1,5-anhydroglucitol + 100 mg galactose |
| None (control) | (0.036) | 2.00 (0.143) | 18.90 (1.352) |
| Galactokinase method | (0.038) | 2.00 (0.142) | 2.03 (0.144) |
| NAD-dependent galactose dehydrogenase method | (0.039) | 2.00 (0.143) | 2.00 (0.143) |
| NADP-dependent galactose dehydrogenase method | (0.037) | 2.00 (0.144) | 2.01 (0.145) |
| Galactose oxidase method | (0.036) | 2.00 (0.144) | 2.08 (0.150) |

Table 1 shows that, in the presence of galactose, the amount of 1,5-anhydroglucitol can be precisely determined only by the methods according to the present invention.

TEST EXAMPLE 2

The experiment was carried out using three types of samples: (1) purified water, (2) 2 mg/dl 1,5-anhydroglucitol, and (3) 2 mg/dl 1,5-anhydroglucitol containing 100 mg/dl galactose. The amount of 1,5-anhydroglucitol in the test samples was determined by the methods described in Example 13 (the galactokinase method), Example 14 (the NAD-dependent galactose dehydrogenase method), Example 15 (the NADP-dependent galactose dehydrogenase method), and Example 16 (the galactose oxidase method). As a control experiment, the amount of 1,5-anhydroglucitol in the test samples was determined by the same method as in Example 13 except that galactokinase, ATP and magnesium chloride were not contained in Reagent solution 3. The results are shown in Table 2.

TABLE 2

| Method of pretreatment | 1,5-anhydroglucitol content (mg) (OD value) | | |
|---|---|---|---|
| | Blank | 2 mg 1,5-anhydroglucitol | 2 mg 1,5-anhydroglucitol + 100 mg galactose |
| None (control) | (0.035) | 2.00 (0.141) | 17.82 (1.256) |
| Galactokinase method | (0.036) | 2.00 (0.143) | 2.03 (0.145) |
| NAD-dependent galactose dehydrogenase method | (0.038) | 2.00 (0.144) | 2.00 (0.144) |
| NADP-dependent galactose dehydrogenase method | (0.035) | 2.00 (0.143) | 1.99 (0.142) |
| Galactose oxidase method | (0.037) | 2.00 (0.142) | 2.13 (0.151) |

Table 2 shows that, in the presence of galactose, the amount of 1,5-anhydroglucitol can be precisely determined only by the methods according to the present invention.

Certain embodiments of the present invention are illustrated in the following examples.

EXAMPLE 1

(Combined Use of the Hexokinase Method for Elimination of Glucose and the Galactokinase Method for Elimination of galactose)

Reagent solutions having the following compositions were prepared and used in the reactions described below.

| Reagent solution 1 | |
|---|---|
| 25 mM phosphate buffer solution (pH 7.5) | 50 ml |
| Sodium chloride | 50 mM |
| Galactokinase | 20 units/ml |
| ATP | 5 mg/ml |
| Magnesium chloride | 4.9 mM |
| Hexokinase | 3.2 units/ml |
| Phosphohexose isomerase | 20 units/ml |
| 6-phosphofructokinase | 20 units/ml |
| Peroxidase | 10 units/ml |
| Reagent solution 2 | |
| 200 mM phosphate buffer solution (pH 6.0) | 20 ml |
| Phenol | 0.1 mg/ml |
| Pyranose oxidase | 100 units/ml |
| BCMA | 0.1 mg/ml |

A standard solution of 1,5-anhydroglucitol (product of Sigma Co.) was diluted with purified water to prepare 1,5-anhydroglucitol standard dilutions (5, 2, 1, 0.5 and 0.25 mg/dl). Reagent solution 1 (2.25 ml) was added to 0.05 ml of each of the dilutions and to 0.05 ml of distilled water as the blank, and the reaction was carried out at 37° C. for 10 minutes. Then, 0.75 ml of Reagent solution 2 was added thereto and the reaction was carried out at 37° C. for 5 minutes. After the reaction, the absorbance at 755 nm was measured, and a calibration curve was obtained. The calibration curve is shown in FIG. 1.

EXAMPLE 2

The same procedure as in Example 1 was repeated, except that a serum containing 2.53 mg/dl 1,5-anhydroglucitol (determined by colorimetry using a column) was used instead of the 1,5-anhydroglucitol standard dilutions. The amount of 1,5-anhydroglucitol in the serum was calculated based on the absorbance at 755 nm and the calibration curve obtained in Example 1, and was found to be 2.56 mg/dl.

EXAMPLE 3

(Combined Use of the Hexokinase Method for Elimination of Glucose and the NAD-dependent Galactose Dehydrogenase Method for Elimination of Galactose)

Figure 2:
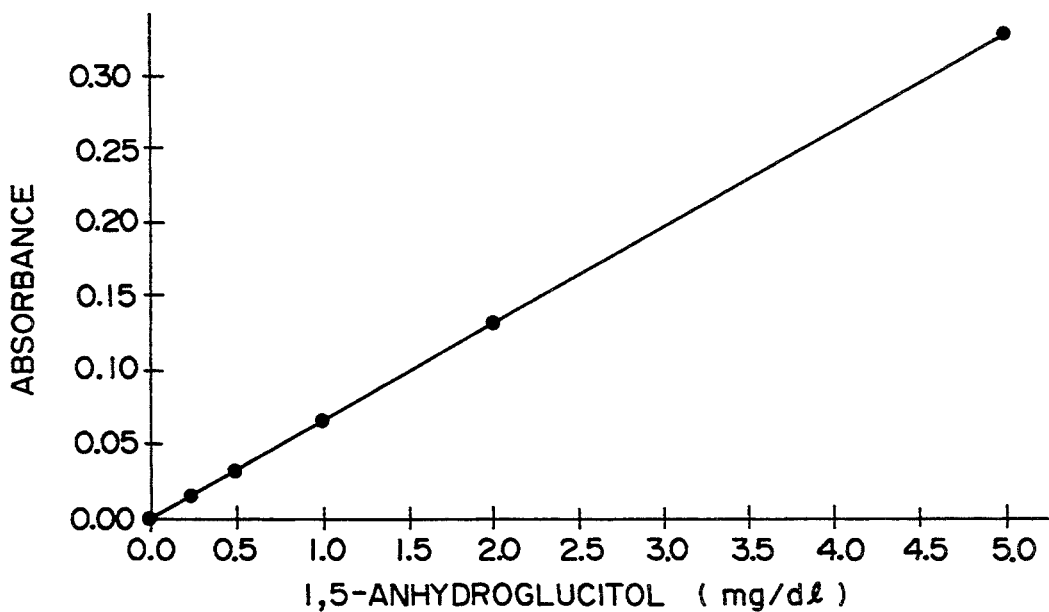
FIG. 2 shows the calibration curve for 1,5-anhydroglucitol obtained by the NAD-dependent galactose dehydrogenase method in combination with the hexokinase method.

The same procedure as in Example 1 was repeated, except that 5 units/ml galactose dehydrogenase (EC 1.1.1.48) and 5 mg/ml NAD were used instead of galactokinase. The obtained calibration curve is shown in FIG. 2.

EXAMPLE 4

The amount of 1,5-anhydroglucitol in the serum used in Example 2 was determined according to the method in Example 3, and was found to be 2.54 mg/dl.

EXAMPLE 5

(Combined Use of the Hexokinase Method for Elimination of Glucose and the NADP-dependent Galactose Dehydrogenase Method for Elimination of Galactose)

Figure 3:
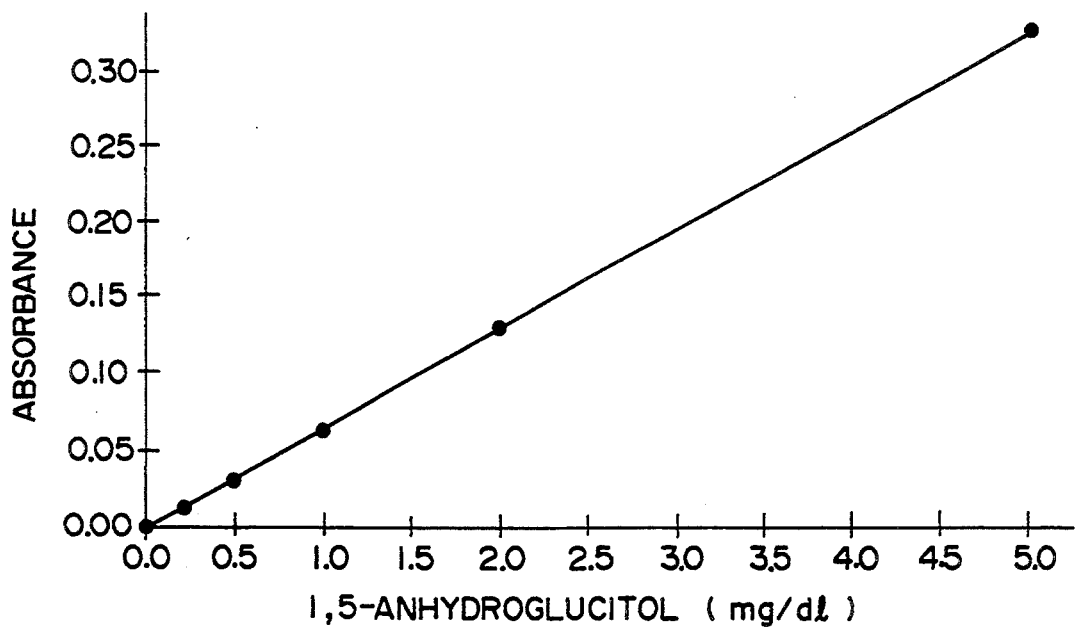
FIG. 3 shows the calibration curve for 1,5-anhydroglucitol obtained by the NADP-dependent galactose dehydrogenase method in combination with the hexokinase method.

The same procedure as in Example 1 was repeated, except that 5 units/ml galactose dehydrogenase (EC 1.1.1.120) and 5 mg/ml NADP were used instead of galactokinase. The obtained calibration curve is shown in FIG. 3.

EXAMPLE 6

The amount of 1,5-anhydroglucitol in the serum used in Example 2 was determined according to the method in Example 5, and was found to be 2.55 mg/dl.

EXAMPLE 7

(Combined Use of the Hexokinase Method for Elimination of Glucose and the Galactose Oxidase Method for Elimination of Galactose)

Figure 4:
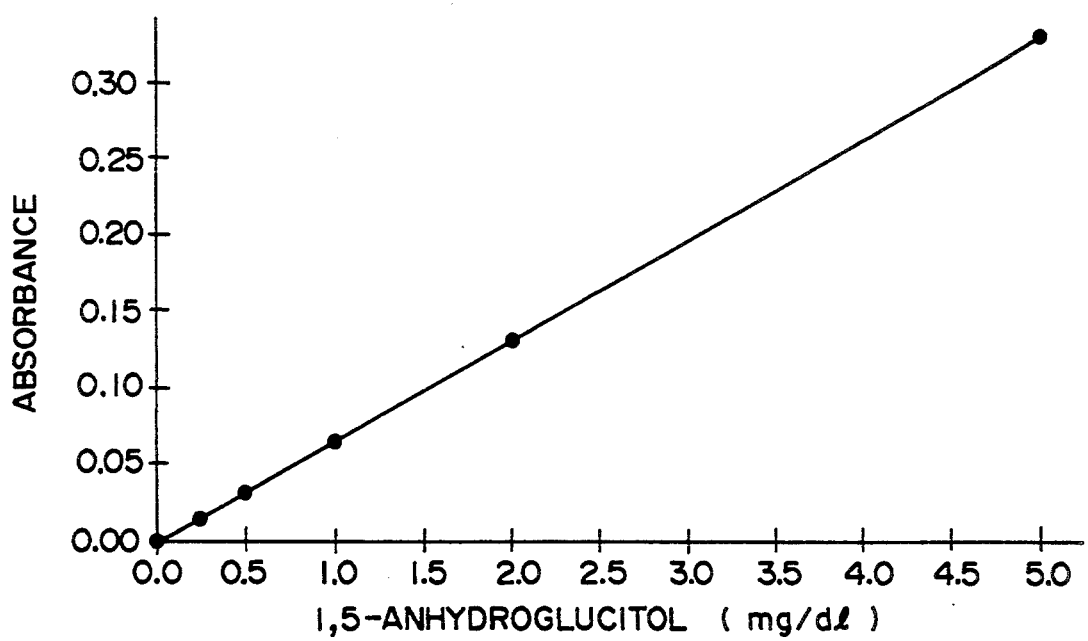
FIG. 4 shows the calibration curve for 1,5-anhydroglucitol obtained by the galactose oxidase method in combination with the hexokinase method.

The same procedure as in Example 1 was repeated, except that 20 units/ml galactose oxidase was used instead of galactokinase. The obtained calibration curve is shown in FIG. 4.

EXAMPLE 8

The amount of 1,5-anhydroglucitol in the serum used in Example 2 was determined according to the method in Example 7, and was found to be 2.60 mg/dl.

EXAMPLE 9

(Combined Use of the Hexokinase Method for Elimination of Glucose and the Galactokinase Method for Elimination of Galactose, with ATP Formation by the Pyruvate Kinase Reaction)

The amount of 1,5-anhydroglucitol in the serum used in Example 2 was determined by the same method as in Example 1, except that the amount of ATP added was reduced to 0.5 mg/ml and 5 units/ml pyruvate kinase and 1 mg/ml phosphoenol pyruvate were added. The amount was determined to be 2.55 mg/dl.

EXAMPLE 10

(Combined Use of the Hexokinase Method for Elimination of Glucose and the Galactokinase Method for Elimination of Galactose, with ATP Formation by the Creatine Kinase Reaction)

The amount of 1,5-anhydroglucitol in the serum used in Example 2 was determined by the same method as in Example 1, except that the amount of ATP added was reduced to 0.5 mg/ml and 10 units/ml creatine kinase and 1 mg/ml of creatine phosphate were added. The amount was determined to be 2.56 mg/dl.

EXAMPLE 11

(Combined Use of the Hexokinase Method for Elimination of Glucose and the Galactokinase Method for Elimination of Galactose, with MCDP)

The amount of 1,5-anhydroglucitol in the serum used in Example 2 was determined by the same method as in Example 1, except that 0.1 mg/ml MCDP was used instead of BCMA. The amount was determined to be 2.52 mg/dl.

EXAMPLE 12

(Combined Use of the Hexokinase Method for Elimination of Glucose and the Galactokinase Method for Elimination of Galactose, with CCAP)

The amount of 1,5-anhydroglucitol in the serum used in Example 2 was determined by the same method as in Example 1, except that 0.1 mg/ml CCAP was used instead of BCMA. The amount was determined to be 2.54 mg/dl.

EXAMPLE 13

(Elimination of galactose by the Galactokinase Method)

Reagent solutions having the following compositions were prepared and used in the reactions described below.

| Reagent solution 3 | |
|---|---|
| 25 mM phosphate buffer solution (pH 7.5) | 50 ml |
| Sodium chloride | 50 mM |
| Galactokinase | 20 units/ml |
| ATP | 5 mg/ml |
| Magnesium chloride | 4.9 mM |
| Peroxidase | 10 units/ml |
| Reagent solution 4 | |
| 200 mM phosphate buffer solution (pH 6.0) | 20 ml |
| Phenol | 0.1 mg/ml |
| Pyranose oxidase | 100 units/ml |
| BCMA | 0.1 mg/ml |

Figure 5:
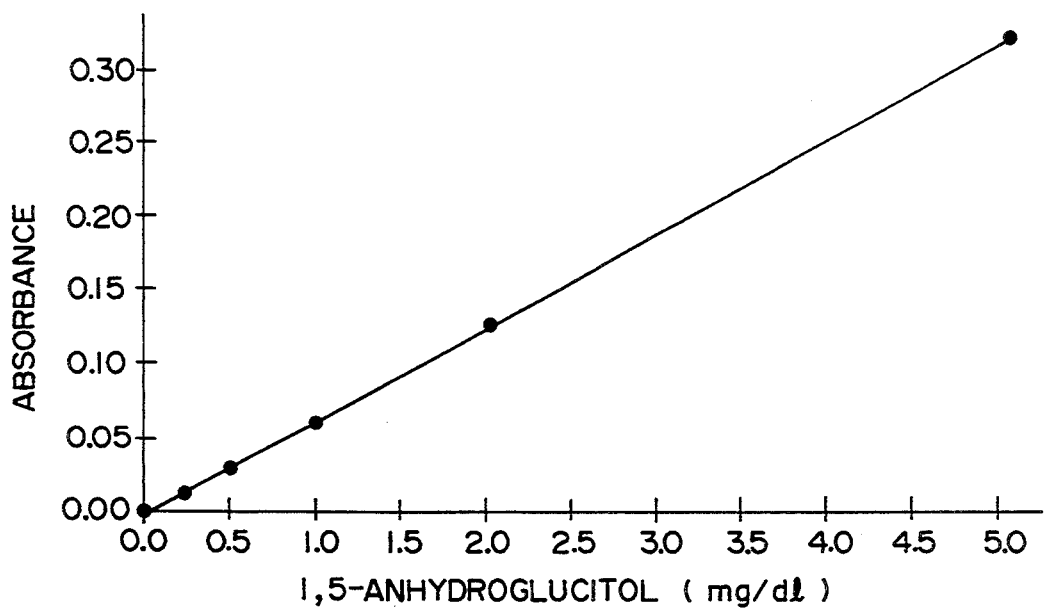
FIG. 5 shows the calibration curve for 1,5-anhydroglucitol obtained by the galactokinase method.

A standard solution of 1,5-anhydroglucitol (product of Sigma Co.) was diluted with purified water to prepare 1,5-anhydroglucitol standard dilutions (5, 2, 1, 0.5 and 0.25 mg/dl). Reagent solution 3 (2.25 ml) was added to 0.05 ml of each of the dilutions and to 0.05 ml of distilled water as the blank, and the reaction with the galactose-eliminating enzyme was carried out at 37° C. for 10 minutes. Then, 0.75 ml of Reagent solution 4 was added thereto, and the reaction with the enzyme for the 1,5-anhydroglucitol determination was carried out at 37° C. for 5 minutes. After the reaction, the absorbance at 755 nm was measured, and a calibration curve was obtained. The calibration curve is shown in FIG. 5.

EXAMPLE 14

(Elimination of galactose by the NAD-dependent galactose dehydrogenase method)

Figure 6:
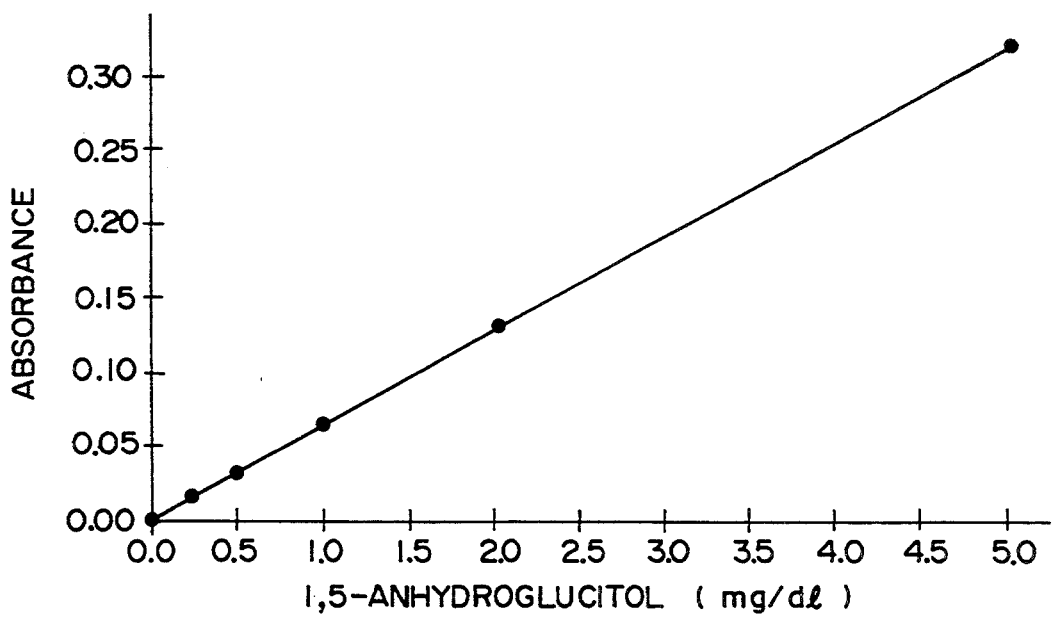
FIG. 6 shows the calibration curve for 1,5-anhydroglucitol obtained by the NAD-dependent galactose dehydrogenase method.

The same procedure as in Example 13 was repeated, except that 5 units/ml galactose dehydrogenase (EC 1.1.1.48) and 5 mg/ml NAD were used instead of galactokinase. The obtained calibration curve is shown in FIG. 6.

EXAMPLE 15

(Elimination of Galactose by the NADP-dependent Galactose Dehydrogenase Method)

Figure 7:
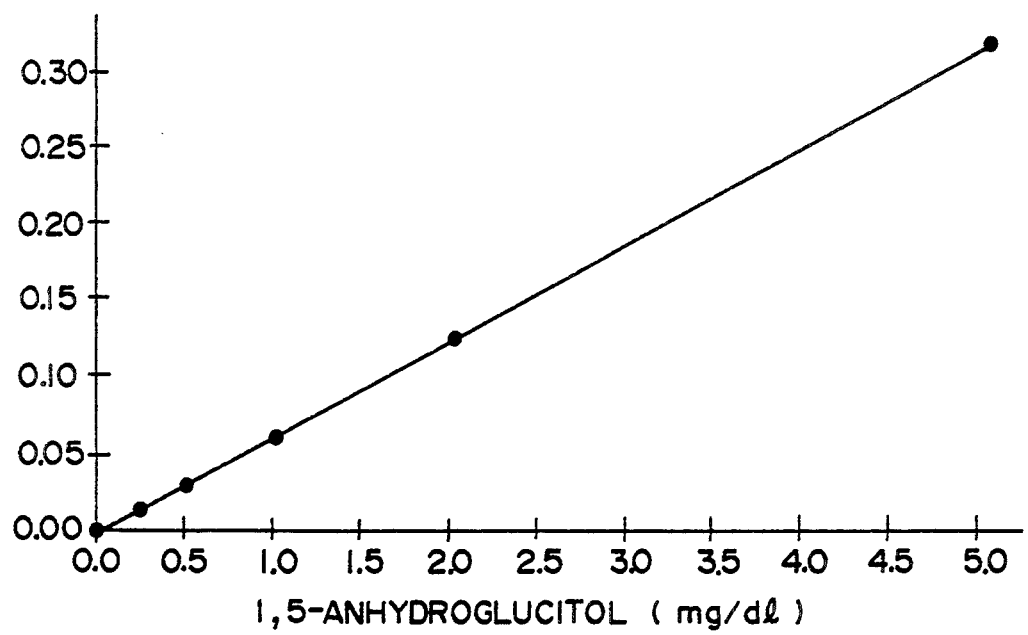
FIG. 7 shows the calibration curve for 1,5-anhydroglucitol obtained by the NADP-dependent galactose dehydrogenase method.

The same procedure as in Example 13 was repeated, except that 5 units/ml galactose dehydrogenase (EC 1.1.1.120) and 5 mg/ml NADP were used instead of galactokinase. The obtained calibration curve is shown in FIG. 7.

EXAMPLE 16

(Elimination of Galactose by the Galactose Oxidase Method)

Figure 8:
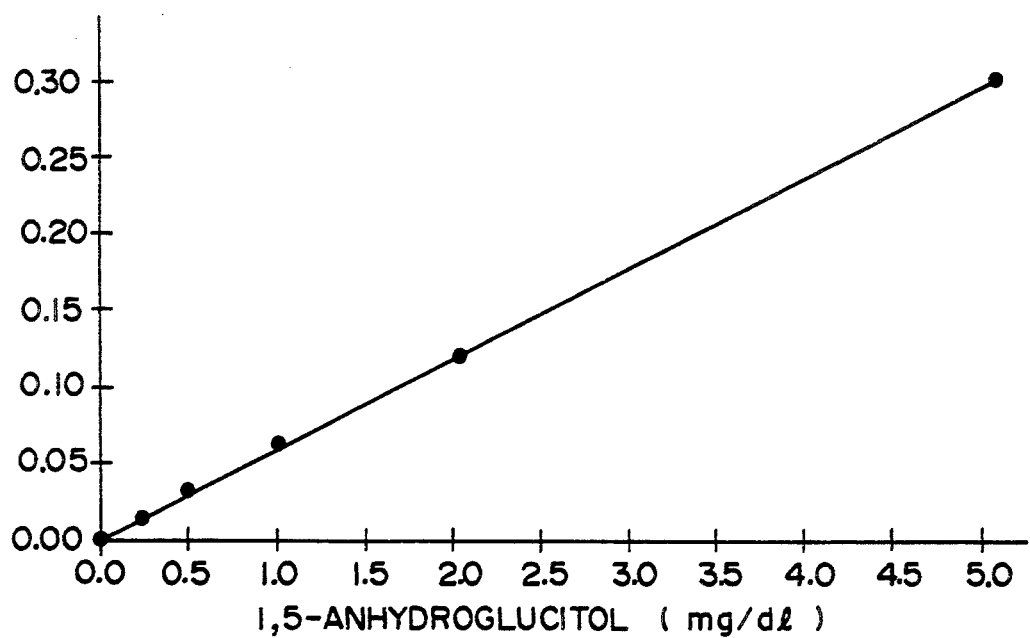
FIG. 8 shows the calibration curve for 1,5-anhydroglucitol obtained by the galactose oxidase method.

The same procedure as in Example 13 was repeated, except that 20 units/ml galactose oxidase was used instead of galactokinase. The obtained calibration curve is shown in FIG. 8.

What is claimed is:

1. A method for quantitatively determining 1,5-anhydroglucitol, fructose or amylase in a sample comprising the steps of:
   first subjecting any galactose present in the sample to a first enzyme reaction selected from the group consisting of galactokinase reaction in the presence of adenosine triphosphate, galactose dehydrogenase reaction in the presence of nicotinamide adenine dinucleotide phosphate or nicotinamide adenine dinucleotode, and galactose oxidase reaction in the presence of oxygen; and thereafter quantitatively determining 1,5-anhydroglucitol, fructose or amylase using a second enzyme reaction different from said first enzyme reaction, wherein said second enzyme reaction also acts on galactose or generates galactose.

2. The method according to claim 1, wherein 1,5-anhydroglucitol is determined by subjecting 1,5-anhydroglucitol to reaction with oxidase, and determining the change in an amount of substrate or product of the oxidase reaction.

3. The method according to claim 1, further comprising the step of subjecting any glucose present in the sample to a third enzyme reaction in which glucose is used as a substrate prior to quantitatively determining said 1,5-anhydroglucitol, fructose or amylase using said second enzyme reaction, wherein said third enzyme reaction is different from said second enzyme reaction.

4. The method according to claim 3, wherein said third enzyme reaction consists of hexokinase reaction, phosphohexose isomerase reaction and 6-phosphofructokinase reaction in the presence of adenosine triphosphate.

* * * * *